United States Patent [19]
Lockett

[11] Patent Number: 5,626,884
[45] Date of Patent: May 6, 1997

[54] TREATMENT OF SICKLE CELL DISEASE

[76] Inventor: Curtis G. Lockett, 3063 N. Galvez St., New Orleans, La. 70117

[21] Appl. No.: 516,737

[22] Filed: Aug. 18, 1995

[51] Int. Cl.⁶ ............... A61K 33/32; A61K 33/24; A61K 33/36; A61K 33/06; A61K 33/04; A61K 35/78; A61K 31/70; A61K 31/51; A61K 31/44; A61K 31/355; A61K 31/34; A61K 31/07

[52] U.S. Cl. ............... 424/639; 424/641; 424/655; 424/667; 424/682; 424/702; 424/195.1; 514/52; 514/276; 514/345; 514/356; 514/458; 514/474; 514/725

[58] Field of Search ............... 424/639, 641, 424/655, 667, 682, 702, 195.1; 514/52, 276, 345, 356, 458, 474, 725

[56] References Cited

U.S. PATENT DOCUMENTS

| | | | |
|---|---|---|---|
| 4,261,980 | 4/1981 | Cort | 424/177 |
| 4,376,766 | 3/1983 | Collinson-Jones et al. | 424/177 |
| 4,629,625 | 12/1986 | Gaull | 424/145 |
| 4,866,052 | 9/1989 | Hider et al. | 514/184 |
| 4,904,678 | 2/1990 | Chima | 514/345 |
| 4,945,083 | 7/1990 | Jansen, Jr. | 514/52 |
| 5,108,754 | 4/1992 | Wilburn | 424/422 |
| 5,114,972 | 5/1992 | Ohnishi | 514/530 |
| 5,364,644 | 11/1994 | Walaszek et al. | 514/574 |

OTHER PUBLICATIONS

NIH Publication No. 89–2117, "Management and Therapy of Sickle Cell Disease," 1989, U.S. Department of Health and Human Services, Charache et al., ed.

Primary Examiner—Raymond Henley, III
Attorney, Agent, or Firm—Richard C. Litman

[57] ABSTRACT

A maintenance regimen with controlled intake of particular vitamin, mineral, and micronutrient formulations, drastically reduces the incidence and severity of sickle cell disease crises. The formulations include vitamin A, vitamin B-1, vitamin B-2, vitamin B-6, vitamin B-12, vitamin C, vitamin D, vitamin E, niacinamide, para-aminobenzoic acid (PABA), pantothenic acid, choline bitartrate, inositol, rutin, citrus bioflavonoid complex, betaine hydrochloride, hesperidin complex, folic acid, biotin, calcium, iron, magnesium, zinc, potassium, manganese, iodine, chromium, selenium, and a pharmaceutically acceptable carrier, provided at or just below critical saturation levels, determined for each individual by carefully monitoring tolerance on titration. The daily dose may exceed that necessary as dietary or nutritional supplements, and trigger an increase in the production of viable hemoglobin, and alters the overall blood profile. Platelet concentration is increased up to twice that of seen in normal blood, and the red blood cells produced display increased resistance to sickling. This enhanced biosynthesis is achieved by providing sufficient stores of precursors that stimulate low level manufacture without substantial feedback control by the upper central nervous system.

4 Claims, No Drawings

TREATMENT OF SICKLE CELL DISEASE

BACKGROUND OF THE INVENTION

1. Field of the Invention

The present invention relates to the treatment and prophylaxis of hemoglobin disorders. More particularly, the present invention provides a tailored preventative and/or maintenance treatment regimen for an individual suffering from genetic sickle cell disease.

2. Description of the Prior Art

As described in NIH Publication No. 89-2117, "Management and Therapy of Sickle Cell Disease, " 1989 herein incorporated, sickle, cell disease is a generic term for a group of genetic disorders characterized by the predominance of hemoglobin S (Hb S). These disorders include sickle cell anemia, the sickle beta thalassemia syndromes, and hemoglobinopathies in which Hb S is in association with another abnormal hemoglobin.

The two beta globin genes located on chromosome 11 and the four alpha globin genes located on chromosome 16 determine hemoglobin production. Normal red blood cells are produced in individuals who carry all four alpha globin genes and two normal beta globin genes ($\beta A$). Carriers of the sickle cell trait, who do not normally physically express the disease, have a normal beta globin gene and a $\beta S$ globin gene, resulting in the production of both normal hemoglobin A and hemoglobin S, with a predominance of Hb A. Individuals who are homozygous for the sickle beta globin gene ($\beta S$) have sickle cell anemia (Hb SS). Individuals with sickle beta thalassemia have a $\beta S$ gene and a gene for beta thalassemia, $\beta$thal. Those who have two abnormal beta globin genes, $\beta S$ and $\beta C$, produce hemoglobins Hb S and Hb C, and have Hb SC disease. The absence of two of the alpha globin genes results in alpha thalassemia. Abnormalities in both the beta and alpha genes may be present in the same individual.

Red blood cells of suffers of sickle cell disease are prone to distortions in geometry when deoxygenated. This distortion arises from the polymerization or gelling of Hb S molecules into elongated microtubular structures. Hb S is more susceptible to polymerization in the deoxygenated state than hemoglobin A due to the substitution of a hydrophobic residue, valine, for a polar residue glutamic acid in Hb A. These distortions of red blood cells, or sickling, leads to chronic hemolytic anemia and vasoocclusion resulting in ischemic tissue injury.

Hemolytic anemia is caused by abnormal properties of Hb S and/or by repeated cycles of sickling and unsickling, which interact to produce irreversible red cell membrane changes and erythrocyte destruction. Tissue injury is usually produced by hypoxia secondary to obstruction of blood vessels by an accumulation of sickled erythrocytes. The organs at greatest risk are those with venous sinuses where blood flow is slow and oxygen tension and pH are low (spleen, kidney, bone marrow) or those with a limited terminal arterial blood supply (eye, head of the femur). Symptoms of the hypoxic injury may be either acute (e.g., painful events, acute chest syndrome) or insidious in onset (e.g.. aseptic necrosis of the hips, sickle cell retinopathy). The effects of acute and chronic tissue injury may ultimately result in organ failure, particularly as the patient ages.

In managing chronic sickle cell disease, conventional maintenance measures usually include preventative administration of antibiotics, hydration, and supplementation of dietary deficiencies. For painful events, analgesics such as aspirin, acetaminophen, ibuprofin, codeine or oxycodone may be administered. More drastic measures, such as blood transfusions or the use of compositions which change the geometry and/or oxygen binding ability of sickled red blood cells have been employed for acute indications.

The use of various vitamins, minerals, and amino acids in treating anemia related disorders has been the subject of earlier patents. For example, U.S. Pat. No. 4,945,083, issued Jul. 31, 1990 to Christian Jansen, Jr. describes a method for treating or preventing macrocytic-megaloblastic anemias with multi-factor vitamin formulations. U.S. Pat. No. 4,261, 980, issued May 14, 1981 to Joseph Cort and U.S. Pat. No. 4,376,766, issued Mar. 15, 1983 to Rosalind Collinson-Jones et al. describe the use of amino acids in sickle cell treatments.

Other combination therapies for sickle cell anemia with formulations that include vitamins are described in U.S. Pat. No. 4,904,678, issued Feb. 27, 1990 to Oji Chima, and U.S. Pat. No. 5,108,754, issued Apr. 28, 1992 to Michael Wilburn. U.S. Pat. No. 4,866,052, issued Sep. 12, 1989 to Robert Hider et al. describes the use of zinc bound to various ligands, including ascorbic acid (vitamin C).

U.S. Pat. No. 5,114,972, issued May 19, 1992 to Tsuyoshi Ohnishi describes the anti-oxidant and anti-cancer activity of prostaglandin derivatives of ascorbic acid. U.S. Pat. No. 4,629,625, issued Dec. 16, 1986 to Gerald Gaull describes compositions including vitamins and/or minerals in combination with taurine, a compound synthesized in animal tissues, useful in providing a protective action on cell membranes. U.S. Pat. No. 5,364,644, issued Nov. 15, 1994 to Zbigniew Walaszek et al. describes methods for lowering cholesterol with D-glucarate which may include a multiplicity of vitamins, minerals and micronutrients.

None of the above inventions and patents, taken either singly or in combination, is seen to describe the instant invention as claimed.

SUMMARY OF THE INVENTION

The present invention is based on the finding that a maintenance regimen with controlled intake of particular vitamin, mineral, and micronutrient formulations, drastically reduces the incidence and severity of sickle cell disease crises. The formulations useful in the present invention include vitamin A, vitamin B-1, vitamin B-2, vitamin B-6, vitamin B-12, vitamin C, vitamin D, vitamin E, niacinamide, para-aminobenzoic acid (PABA), pantothenic acid, choline bitartrate, inositol, rutin, citrus bioflavonoid complex, betaine hydrochloride, hesperidin complex, folic acid, biotin, calcium, iron, magnesium, zinc, potassium, manganese, iodine, chromium, selenium, and a pharmaceutically acceptable carrier.

These vitamins and minerals are administered at or just below critical saturation levels which may be determined for each individual by establishing a base line dosage level of multiple vitamins and minerals over a period of days; adjusting this base line dosage upwards until the manifestation of easily observed responses; and finally reducing the dosage slightly until such manifestations disappear. Accordingly, the daily doses for some of these vitamin, minerals, and micronutrients will exceed those conventionally considered necessary as dietary or nutritional supplements The present method triggers an increase in the production of viable hemoglobin, and alters the overall blood profile. Platelet concentration is increased up to about twice that observed in normal blood, and the red blood cells produced display increased resistance to sickling. This enhanced biosynthesis is achieved by providing sufficient stores of precursors that stimulate low level manufacture without substantial feedback control by the upper central nervous system.

Accordingly, it is a principal object of the invention to provide a treatment for sickle cell anemia and related disorders with a composition that includes multiple vitamins and minerals.

It is another object of the invention to provide an approach to treatment wherein dosage is critically controlled based on close monitoring of expressed responses for each individual.

It is a further object of the invention to provide a treatment regimen which may be administered in the home environment without expensive equipment.

These and other objects of the present invention will become readily apparent upon further review of the following specification.

DETAILED DESCRIPTION OF THE INVENTION

The present invention provides a method of treating persons having sickle cell disease. The effective daily dosage at saturation of each vitamin or mineral falls within the following ranges:

| | |
|---|---|
| Vitamin A | 8,250–250,000 I.U. |
| Vitamin B-1 | 25–1000 mg. |
| Vitamin B-2 | 25–1000 mg. |
| Vitamin B-6 | 25–1000 mg. |
| Vitamin B-12 | 25–1000 mcg. |
| Vitamin C | 25–1000 mg. |
| Vitamin D | 100–4000 I.U. |
| Vitamin E | 25–1000 I.U. |
| Niacinamide | 25–1000 mg. |
| Para-aminobenzoic acid (PABA) | 25–1000 mg. |
| Pantothenic Acid | 25–1000 mg. |
| Choline Bitartrate | 25–1000 mg. |
| Inositol | 25–1000 mg. |
| Rutin | 8.25–250 mg. |
| Citrus Bioflavonoid Complex | 8.25–250 mg. |
| Betaine Hydrochloride | 8.25–250 mg. |
| Hesperidin Complex | 1.25–50 mg. |
| Folic Acid | 100–4000 mcg. |
| Biotin | 25–1000 mcg. |
| Calcium | 10–400 mg. |
| Iron | 8.25–250 mg. |
| Magnesium | 5–100 mg. |
| Zinc | 5–100 mg. |
| Potassium | 3.75–150 mg. |
| Manganese | 1.5–60 mg. |
| Iodine | 37.5–1500 mcg. |
| Chromium | 3.75–150 mcg. |
| Selenium | 2.5–100 mcg. |

It is preferable to more closely tailor the present method to a particular individual, to insure that saturation levels are administered and maintained. Conventionally employed determinations of dosage based on body weight may be unreliable in providing the necessary dosage, as each individual responds at different dosages uncorrelated with weight. However, age may be used to select a useful starting point for determining an effective daily dosage level.

The normal range of conditions for body surface temperature, frequency of urination, sleep and physical activity should be established prior to practicing the present method. Persons of six years of age or younger should start with the minimum dosage listed above, those of from 7–15 years of age, twice that amount, and those over 15 years of age four times that amount. This selected base daily dosage is administered for an initial period of from 3–10 days, and the conditions established for the person are monitored. Deviations outside the established range for these conditions indicate that saturation has been surpassed, and the dosage should be reduced, preferably by up to half.

After this initial period, the base daily dosage may be gradually adjusted upward to a modified daily dosage with each succeeding 3–10 day period, in increments of from about 1 to about 100 percent, if the above noted conditions stay within the normal range established. Should the conditions in any period deviate outside the established range, a downward adjustment of about 1 to 50 percent should be made. Preferably, the relative proportions of these components is maintained as the dosage is increased or decreased.

In particular, an increase in urination rate to twice normal, loss of sleep, marked hyperactivity, and/or a perceptible increase in the body surface temperature of the skin to the touch without any systemic fever indicate that the saturation level has been surpassed. Though a brightening of the eyes is a normal effect of the present inventive method, an overnight loss of tint in the whites of the eyes during the initial period or any subsequent period may be also used as an indication to reduce the dosage.

The increments chosen for each succeeding modified daily dosage should be reduced until a first modified daily dosage is found, in which no deviation of conditions outside the normal range is perceived. The first modified daily dosage is within from about 1 to 10 percent of a second modified dosage in which conditions deviate beyond normal. At that point, the first modified daily dosage is selected and used for continuous administration.

Sustained-release formulations of the above ingredients, such as polymer matrix tablets and liquid gel compositions may be used, and are ideally suited for maintaining a dosage at or near saturation level, once determined. These formulations may include an inert pharmaceutically acceptable carrier. Preferably, the carrier is a base selected from one or more of rice, papaya, watercress, parsley, kelp, alfalfa, cabbage, cherry, wheat flour, and bromelain.

Mineral ingredients are preferably provided as amino acid chelates. Trace amounts of additional chelated minerals may also be present, including actinium, aluminum, antimony, barium, beryllium, bismuth, boron, bromine, cadmium, cerium, cesium, chlorine, cobalt, copper, dysprosium, erbium, europium, fluorine, gadolinium, gallium, germanium, gold, hafnium, holmium, indium, iridium, lanthanum, lithium, lutetium, molybdenum, neodymium, nickel, niobium, osmium, palladium, phosphorous, platinum, praseodymium, rhenium, rhodium, rubidium, ruthenium, samarium, scandium, silicon, silver, sodium, strontium, sulfur, tantalum, tellurium, terbium, thallium, thorium, tin, titanium, tungsten, uranium, vanadium, ytterbium, yttrium, and zirconium.

To assist in determining and administering the saturation level dosage to a person having sickle cell disease, a kit may be used that includes individual tablets or capsules each with the minimum amounts, or integer factor thereof, of the vitamins, minerals, and micronutrients, already in combination, and in a suitable pharmaceutical carrier. For insuring proper monitoring the present process, forms and/or charts may be provided that include space for recordation of conditions at associated daily doses. This kit may further include detailed instructions for carrying out the present method in any appropriate media, as well as any information regarding the formulation.

The administration of a daily saturation dosage when continuously maintained provides an effective sickle cell crisis preventative measure that may be practiced outside a critical care environment. This allows persons suffering from sickle cell disease to lead more productive, normal lives. The constant threat of crisis onset is dramatically reduced, thereby contributing to greater mental and emotional confidence.

The exact pharmacodynamic and/or biochemical mechanisms by which the present method is effective have not been established. However, a clearly observed increase in the production of viable hemoglobin and platelets indicates that a low level adjustment in blood cell production is triggered as the saturation level is approached. The oxygen carrying capacity of the blood per volume is accordingly increased, and sickle cell crises based on oxygen deficiencies is substantially eliminated. In addition, the immune system is significantly enhanced, thereby reducing the need for additional medication, such as antibiotics and analgesics, normally used in sickle cell disease management.

When the daily saturation level is exceeded, however, these positive effects were observed to be substantially reduced. An upper CNS feedback response may be indicated for this edge phenomena, and should be avoided. It is therefore a critical aspect of the present invention to maintain the fine balance at or just below a daily saturation level.

EXAMPLE

A patient diagnosed with Sickle Cell Anemia was treated with conventional methods including the use of transfusions, antibiotics, acetaminophen, and codeine. Despite these treatments sickle cell crises were frequent, resulting in hospitalizations for severe fevers and multiple organ failures.

At age 7, all conventional treatments were ceased, and an experimental daily dosage "A" was established according to the present invention, monitoring hyperactivity, urination rate, eye color, and body temperature. Sickle cell crises were drastically reduced and no hospitalizations were required while the present method was practiced. The daily dosages were periodically reevaluated, and adjusted. Dosages "B" and "C" were the levels established at age 13 and 18, respectively.

| Component | Dosage A | Dosage B | Dosage C |
| --- | --- | --- | --- |
| Vitamin A | 1.5 mg. | 3.0 mg. | 4.5 mg. |
| Vitamin B-1 | 50.0 mg. | 100.0 mg. | 150.0 mg. |
| Vitamin B-2 | 50.0 mg. | 100.0 mg. | 150.0 mg. |
| Vitamin B-6 | 50.0 mg. | 100.0 mg. | 150.0 mg. |
| Vitamin B-12 | 0.05 mg. | 0.10 mg. | 0.15 mg. |
| Vitamin C | 50.0 mg. | 100.0 mg. | 150.0 mg. |
| Vitamin D | .012 mg. | .025 mg. | .0375 mg. |
| Vitamin E | 43.4 mg. | 86.7 mg. | 130.0 mg. |
| Niacinamide | 50.0 mg. | 100.0 mg. | 150.0 mg. |
| Para-aminobenzoic acid (PABA) | 50.0 mg. | 100.0 mg. | 150.0 mg. |
| Pantothenic Acid | 50.0 mg. | 100.0 mg. | 150.0 mg. |
| Choline Bitartrate | 50.0 mg. | 100.0 mg. | 150.0 mg. |
| Inositol | 50.0 mg. | 100.0 mg. | 150.0 mg. |
| Rutin | 12.5 mg. | 25.0 mg. | 37.5 mg. |
| Citrus Bioflavonoid Complex | 12.5 mg. | 25.0 mg. | 37.5 mg. |
| Betaine Hydrochloride | 12.5 mg. | 25.0 mg. | 37.5 mg. |
| Hesperidin Complex | 2.5 mg. | 5.0 mg. | 7.5 mg. |
| Folic Acid | 0.2 mg. | 0.4 mg. | 0.6 mg. |
| Biotin | 0.05 mg. | 0.10 mg. | 0.15 mg. |
| Calcium | 10.0 mg. | 20.0 mg. | 30.0 mg. |
| Iron | 12.5 mg. | 25.0 mg. | 37.5 mg. |
| Magnesium | 10.0 mg. | 20.0 mg. | 30.0 mg. |
| Zinc | 10.0 mg. | 20.0 mg. | 30.0 mg. |
| Potassium | 7.5 mg. | 15.0 mg. | 22.5 mg. |
| Manganese | 3.0 mg. | 6.1 mg. | 9.1 mg. |
| Iodine | .075 mg. | 0.15 mg. | 0.23 mg. |
| Chromium | .0075 mg. | 0.015 mg. | 0.023 mg. |
| Selenium | .005 mg. | 0.01 mg. | 0.015 mg. |

At age 14, this daily dosage regimen was temporarily interrupted under medical direction, and conventional treatment was reinstated. Within a few days, sickle cell crises returned in a frequency and at a level of severity at least as great as encountered before age 7, resulting in retinal detachment, and the loss of one of the patient's eyes. Conventional treatment was again ceased and experimental daily dosage "B" was administered. Again, sickle cell crises were drastically reduced and no additional hospitalizations were required while practicing the present regimen.

It is to be understood that the present invention is not limited to the embodiments described above, but encompasses any and all embodiments within the scope of the following claims.

I claim:

1. A method for treating or preventing sickle cell crises in a person having sickle cell disease which comprises administering to said person a cumulative daily dosage of from about 8,250 to 250,000 I.U. vitamin A; from about 25 to 1000 mg. each of vitamin B-1, vitamin B-2, vitamin B-6, vitamin C, niacinamide, para-aminobenzoic acid, pantothenic acid, choline bitartrate, and inositol; from about 25 to 1000 mcg. each of vitamin B-12 and biotin; from about 100 to 4000 I.U. of vitamin D; from about 100–4000 mcg. of folic acid; from about 25 to 1000 I.U. of vitamin E; from about 8.25 to 250 mg. each of rutin, citrus bioflavonoid complex, betaine hydrochloride, and iron; from about 1.25 to 50 mg. of hesperidin complex, from about 10 to 400 mg. of calcium; from about 5 to 100 mg. of magnesium; from about 5 to 100 mg. of zinc; from about 3.75–150 mg. of potassium; from about 1.5 to 60 mg. of manganese; from about 37.5 to 1500 mcg. of iodine; from about 3.75 to 150 mcg. of chromium; and from 2.5–100 mcg. of selenium.

2. The method according to claim 1, wherein said cumulative daily dosage is supplied in the form of sustained-release pharmaceutical compositions consisting essentially of from about 8,250 to 250,000 I.U. vitamin A; from about 25 to 1000 mg. each of vitamin B-1, vitamin B-2, vitamin B-6, vitamin C, niacinamide, para-aminobenzoic acid, pantothenic acid, choline bitartrate, and inositol; from about 25 to 1000 mcg. each of vitamin B-12 and biotin; from about 100 to 4000 I.U. of vitamin D; from about 100–4000 mcg. of folic acid; from about 25 to 1000 I.U. of vitamin E; from about 8.25 to 250 mg of each of rutin, citrus bioflavonoid complex, betaine hydrochloride, and iron; from about 1.25 to 50 mg. of hesperidin complex, from about 10 to 400 mg. of calcium; from about 5 to 100 mg. of magnesium; from about 5 to 100 mg. of zinc; from about 3.75–150 mg. of potassium; from about 1.5 to 60 mg. of manganese; from about 37.5 to 1500 mcg. of iodine; from about 3.75 to 150 mcg. of chromium; from 2.5–100 mcg. of selenium; and a pharmaceutically acceptable carrier.

3. The method according to claim 2, wherein said composition is administered substantially at a daily saturation dosage, wherein said daily saturation dosage is determined by additional preliminary steps of:

a) establishing a normal range for at least one condition selected from the group consisting of frequency of urination, sleep, physical activity, and combinations thereof, for said person;

b) selecting a base daily dosage of a composition consisting essentially of vitamin A, vitamin B-1, vitamin B-2, vitamin B-6, vitamin B-12, vitamin C, vitamin D, vitamin E, niacinamide, paraaminobenzoic acid (PABA), pantothenic acid, choline bitartrate, inositol, rutin, citrus bioflavonoid complex, betaine hydrochloride, hesperidin complex, folic acid, biotin, calcium, iron, magnesium, zinc, potassium, manganese, iodine, chromium, selenium, and a pharmaceutically acceptable carrier;

c) administering to said person having sickle cell disease said base daily dosage for an initial period of from about three to about ten days;

d) continuously monitoring said condition of said person;

e) adjusting said daily dosage upward in increments of from about 1 to 100 percent if said monitoring reveals no deviation of conditions outside the established normal range, and downward by increments of from 1 to 50 percent if said monitoring reveals a perceptible deviation of conditions outside the established normal range, thereby establishing a modified daily dosage;

f) administering to said person having sickle cell disease said modified daily dosage for an additional period of from about 3 to about 10 days;

g) repeating steps d)–f), decreasing succeeding adjusted increments, until a first modified daily dosage in which monitoring reveals no deviation of conditions outside the normal range and a second modified dosage in which monitoring reveals deviation of conditions outside the normal range are within from about 1 to 10 percent of each other; and h) selecting said first modified daily dosage as said daily saturation dosage.

4. The method according to claim 3, wherein the daily saturation dosage is provided in at least one unit dose of said sustained release composition, each said unit dose containing from 8,250 to 25,000 I.U. vitamin A; from about 25 to 100 mg. each of vitamin B-1, vitamin B-2, vitamin B-6, vitamin C, niacinamide, para-aminobenzoic acid, pantothenic acid, choline bitartrate, and inositol; from about 25 to 100 mcg. each of vitamin B-12 and biotin; from about 100 to 400 I.U. of vitamin D; from about 100–4000 mcg. of folic acid; from about 25 to 100 I.U. of vitamin E; from about 8.25 to 25 mg. each of rutin, citrus bioflavonoid complex, betaine hydrochloride, and iron; from about 1.25 to 5 mg. of hesperidin complex, from about 10 to 40 mg. of calcium; from about 5 to 10 mg. of magnesium; from about 5 to 10 mg. of zinc; from about 3.75–15 mg. of potassium; from about 1.5 to 6 mg. of manganese; from about 37.5 to 150 mcg. of iodine; from about 3.75 to 15 mcg. of chromium; and from 2.5–10 mcg. of selenium.

* * * * *